United States Patent
Wright

(10) Patent No.: US 9,527,077 B2
(45) Date of Patent: Dec. 27, 2016

(54) DIAGNOSTIC CARTRIDGE, FLUID STORAGE AND DELIVERY APPARATUS THEREFOR AND METHODS OF CONSTRUCTION THEREOF

(71) Applicant: David W. Wright, Littleton, CO (US)

(72) Inventor: David W. Wright, Littleton, CO (US)

(*) Notice: Subject to any disclaimer, the term of this patent is extended or adjusted under 35 U.S.C. 154(b) by 0 days.

(21) Appl. No.: 14/609,259

(22) Filed: Jan. 29, 2015

(65) Prior Publication Data
US 2016/0220994 A1 Aug. 4, 2016

(51) Int. Cl.
*G01N 21/75* (2006.01)
*B01L 3/00* (2006.01)
*A61B 5/15* (2006.01)
*A61B 5/157* (2006.01)

(52) U.S. Cl.
CPC .......... *B01L 3/502707* (2013.01); *A61B 5/157* (2013.01); *A61B 5/150022* (2013.01); *A61B 5/150221* (2013.01); *A61B 5/150358* (2013.01); *A61B 5/150755* (2013.01); *A61B 5/150274* (2013.01); *A61B 2562/0295* (2013.01); *B01L 2200/028* (2013.01); *B01L 2200/10* (2013.01); *B01L 2300/047* (2013.01); *B01L 2300/0887* (2013.01); *B01L 2300/123* (2013.01); *B01L 2400/0633* (2013.01)

(58) Field of Classification Search
CPC .................... B01L 3/502707; B01L 2300/047; B01L 2200/028; B01L 2300/0887; B01L 2200/10; B01L 2400/0633; B01L 2300/123; A61B 5/150022; A61B 5/150221; A61B 5/150358; A61B 5/150755; A61B 5/157; A61B 5/1502
See application file for complete search history.

(56) References Cited

U.S. PATENT DOCUMENTS

2013/0288257 A1* 10/2013 Wright .................. C12Q 1/686
435/6.12
2014/0322706 A1* 10/2014 Kayyem ........... B01L 3/502715
435/6.11

FOREIGN PATENT DOCUMENTS

EP 2 733 356 A1 5/2014

* cited by examiner

*Primary Examiner* — Dennis M White

(57) ABSTRACT

A disposable, point-of-care diagnostic cartridge has a base with a reaction chamber and an inlet and a fluidic channel extending therebetween. An apparatus is fixed to the base. The apparatus includes a flexible upper layer having a reservoir containing fluid therein; a flexible lower layer, and a rigid substrate sandwiched between the upper and lower layers. The upper layer is fixed to the substrate with a first adhesive having a first bond force. The lower layer has a valve member in fluid communication with a through port in the base and the base inlet. The valve member has a closed state to seal off the through port and the inlet from fluid communication and an open state to bring the through port and the inlet into fluid communication. The valve member is moveable from the closed state to the open state under a force less than the first bond force.

14 Claims, 7 Drawing Sheets

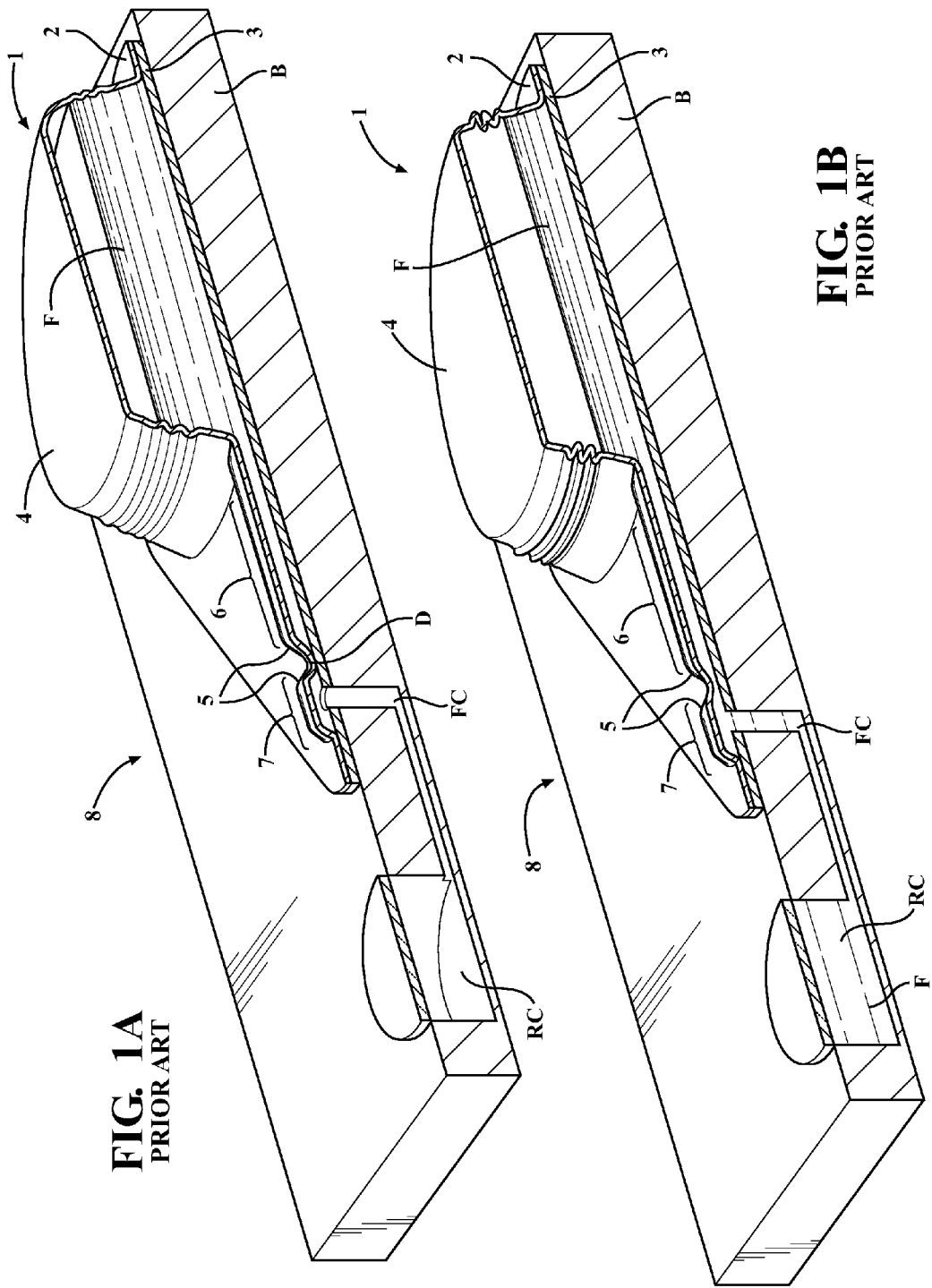

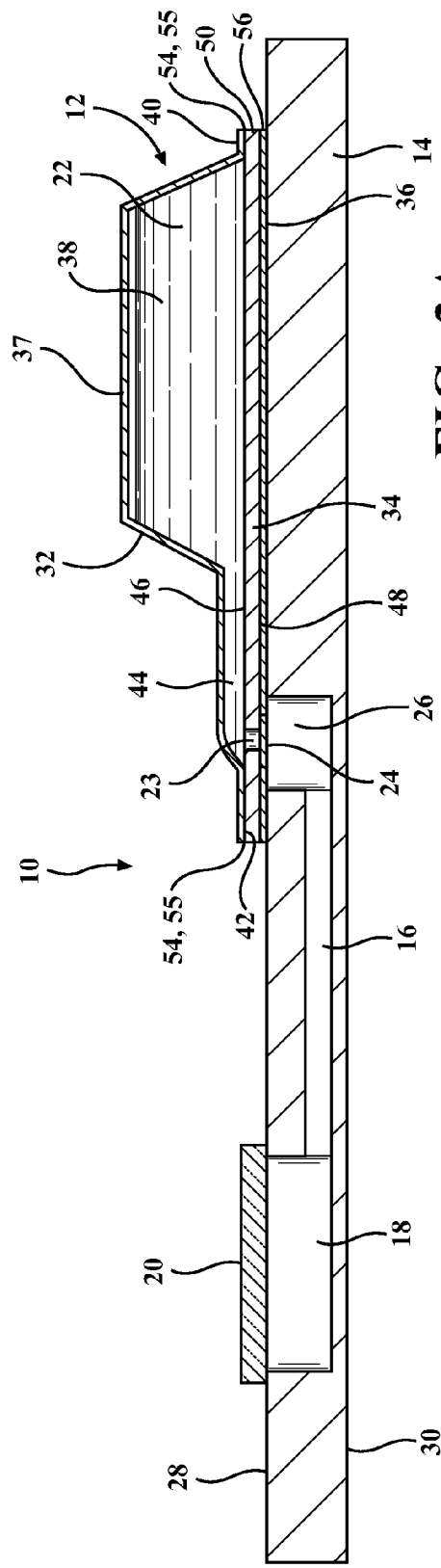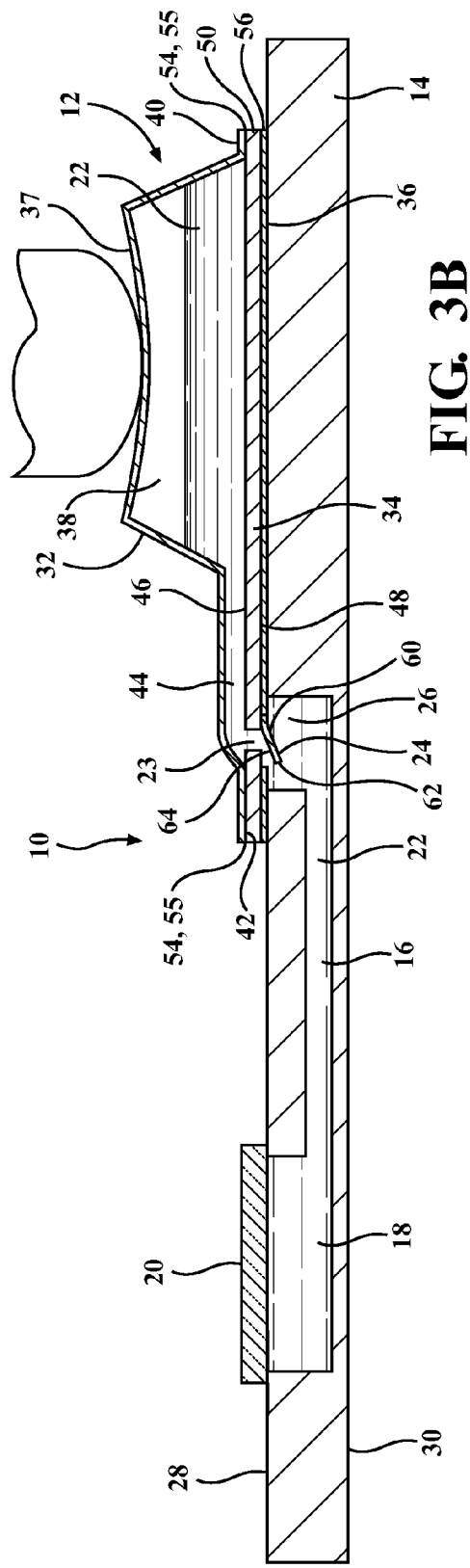

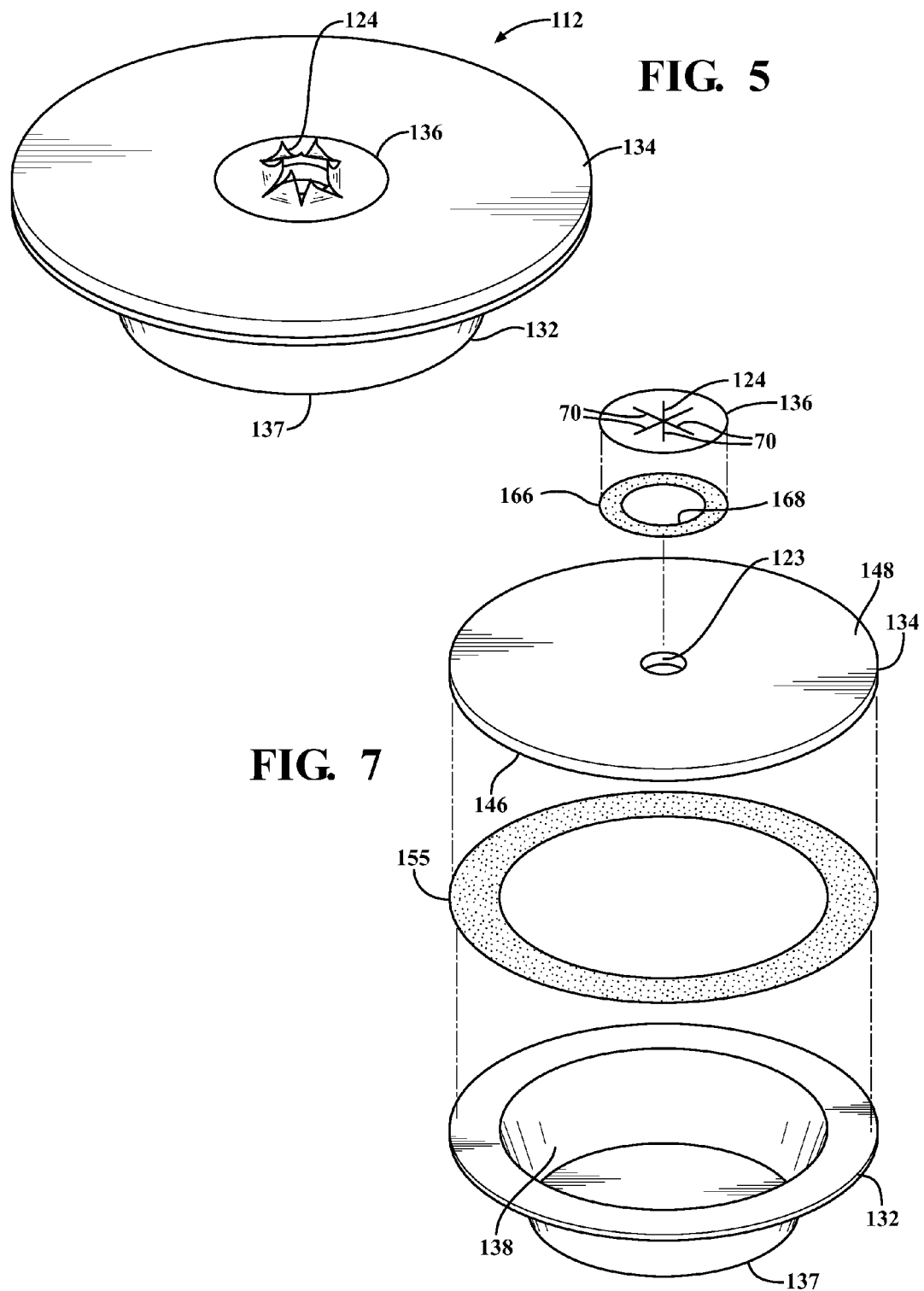

DIAGNOSTIC CARTRIDGE, FLUID STORAGE AND DELIVERY APPARATUS THEREFOR AND METHODS OF CONSTRUCTION THEREOF

BACKGROUND

1. Technical Field

This invention relates generally to in-vitro diagnostics, and more particularly to disposable diagnostic cartridges and apparatus and methods for storing and delivering fluid to a diagnostic cartridge.

2. Related Art

Diagnostic tests are increasingly being used to determine the state or condition of a biological environment, such as in human healthcare, agriculture, live stock management, municipal systems management, and national defense, by way of example and without limitation. A new market is emerging wherein diagnostic tests are being performed at the point-of-care. The diagnostic test can be complex, requiring multiple fluids and multiple steps to execute an assay. An assay is a sequence of steps or procedures used measure the presence or absence of a substance in a sample, the amount of a substance in a sample, or the characteristics of a sample. An example of a common and relative simple point-of-care assay, which can be readily conducted by a layperson, is a blood glucose test. In this test, generally speaking, the blood is mixed with glucose oxidase, which reacts with the glucose in the sample, creating gluconic acid, wherein the gluconic acid reacts with a chemical, typically ferricyanide, producing ferrocyanide. Current is passed through the ferrocyanide and the impedance reflects the amount of glucose present.

Although the aforementioned blood glucose assay is relative common and simple, many assays are far more complex, in that they require specific fluids, often of differing types and quantities, to be stored for future use on the diagnostic device. These fluids may be, but are not limited to, a buffer solution for dilution, fluids containing antibodies and antigens, microspheres coated with binding agents, cell lysing agents, and other fluids required to manipulate the sample being tested. Diagnostic tests that utilize millifluidic and microfluidic volumes of the fluids are intended to provide an incredibly high degree of specificity, sensitivity, and a precise volume and rate of fluid delivery to achieve as accurate a test result as possible. Nearly all microfluidic tests require the introduction of fluids throughout the assay sequence to manipulate the sample being tested and to produce an accurate diagnosis.

Typically, consumable diagnostic devices, meaning the diagnostic device is disposable upon being used, require a companion durable hardware device that interfaces with the consumable diagnostic device to execute the test. The durable hardware performs many functions, one of which is to facilitate dispensing the fluids contained in a reservoir or reservoirs on the consumable diagnostic device into microfluidic or millifluidic channels formed within the consumable diagnostic device. Upon being urged to flow out of the reservoirs, the fluids can flow into a specimen containing reaction chamber. The introduction of the fluids to the reaction chamber requires precision; including flow rate, volume and timing, so as to best replicate the protocols of a laboratory where precession pipettes are employed.

Consumable diagnostic devices commonly include multiple fluid containing reservoirs, sometimes referred to as pouches, and more commonly referred to as blisters, sealed from environmental elements with the fluid being contained within the blister until the time of use. Several techniques have been devised to open the blisters to enable the fluid contained therein to be channeled to a reaction chamber. These techniques usually employ a mechanism that collapses, or crushes the blister under force, and a mechanism that forms an opening exiting the blister, thereby allowing the fluid to be pumped under force out of the blister, through the opening, and throughout the fluidic channels of the diagnostic device to the desired reaction chamber or chambers. The mechanism crushing the blister is typically performed slowly and continuously; however, the mechanism that forms the opening typically results in an uncontrolled "in-rush" of the fluid from the blister to the fluidic channels, which can be disruptive or destructive to the process, thereby having a negative impact on the ability to obtain accurate, reliable test results. This problem is compounded when multiple blisters are being crushed and opened in sequence or in parallel with one another, which is commonly done to promote mixing the fluids from the different blisters with one another, given multiple blister ruptures results in the uncontrolled in-rush of the various fluids from their respective ruptured blisters. Further yet, aside from the undesirable "in-rush" phenomenon, blisters can malfunction as a result of unwanted "delamination" of the blister.

The problem of "in-rush" results from the known construction the blisters. Currently, as shown in FIG. 1, with only a single blister assembly 1 being illustrated for simplicity, known blister assemblies are formed from a lamination of upper and lower film or flexible foil layers 2, 3 with one another, such as via a hot melt adhesive sandwiched therebetween, to form a bulbous portion, commonly referred to as blister 4, and a narrowed channel portion 5 extending from the bulbous portion 4 in the upper layer 2. The narrowed channel portion 5 has an upstream portion 6 in exposed, open fluid communication with the bulbous portion 4 and a downstream portion 7. The upstream and downstream portions 6, 7 are sealed off from one another by an intervening dam D formed by a portion of the upper and lower layers 2, 3 being locally bonded with one another, wherein the dam D is formed via the same adhesive, such as the aforementioned hot melt adhesive layer, and in the same process used to bond the periphery of the layers 2, 3 to one another. As such, the force required to delaminate and open the dam D is the same as the force required to delaminate the remaining portions of the upper layer 2 from the lower layer 3, including the outer periphery of the upper layer 2 from the lower layer 3.

The preformed blister assembly 1, with fluid contained within the bulbous portion 4, is bonded to an underlying substrate or base B of a diagnostic device 8 (FIGS. 1A, 1B), such that the downstream portion 7 of the channel portion 5 is positioned over a fluidic channel FC in the base B, wherein the fluid channel FC is in fluid communication with a downstream reaction chamber RC. The process of opening the blister assembly 1 typically involves compressing the bulbous portion 4 of the blister assembly 1 under a sufficient force to rupture the dam D, thereby causing an intentional delamination of the dam D, and thus, bringing the upstream portion 6 of the narrowed channel portion 5 into open fluid communication with the downstream portion 7, ultimately causing the fluid F from within the bulbous portion 4 to flow through the fluidic channel FC to the reaction chamber RC. However, this process presents multiple challenges, namely, the ability to control the flow rate of the fluid F from the bulbous portion 4 to the reaction chamber RC, and also, the ability to restrict the delamination of the upper layer 2 from the lower layer 3 to only the region of the dam D, while avoiding delamination elsewhere between the upper and lower layer 2, 3. Typically, the amount of force applied to the bulbous portion 4, often referred to as "actuation force", in order to cause the dam D to delaminate is about 45 lbs or more, and as such, the relatively high actuation force required to rupture the dam D inherently causes a sudden burst of fluid flow past the dam D upon initial delamination thereof, thereby producing in the "in-rush" phenomenon. Further, the relatively high actuation force needed to delaminate the dam D inherently causes delamination between the upper and lower layers 2, 3 in areas other than the dam D, such as about the periphery of the bulbous portion 4, which in turn can result in an unintentional burst or leak from the periphery of the bulbous portion 4, thereby destroying the test. This occurs due to the fact that the dam D is formed by the same adhesive and bonding process that bonds of the upper and lower layers 2, 3 together.

SUMMARY OF THE INVENTION

In accordance with one aspect of the invention, a disposable, point-of-care diagnostic cartridge is provided. The cartridge includes a rigid base having opposite upper and lower surfaces. A reaction chamber is formed between the upper and lower surfaces and an inlet extends into the upper surface with at least one fluidic channel extending in fluid communication with the reaction chamber and the inlet. A fluid storage and delivery apparatus is fixed to the upper surface of the rigid base. The apparatus includes a flexible upper layer, a flexible lower layer, and a rigid substrate having an upper surface and a lower surface sandwiched between the upper and lower layers. The flexible upper layer is fixed to the upper surface of the rigid substrate with a first adhesive having a first bond force. The flexible upper layer has a reservoir with a fluid releasably contained therein. The rigid substrate has a through port in fluid communication with the reservoir. The flexible lower layer has a valve member in fluid communication with the through port and the inlet of the rigid base. The valve member has a closed state wherein the through port and the inlet are sealed off from fluid communication with one another and an open state wherein the through port and the inlet are in fluid communication with one another. The valve member is moveable from the closed state to the open state under a force that is less than the first bond force.

In accordance with another aspect of the invention, the valve member can be releasably bonded to the lower surface of the rigid substrate with a second adhesive having a second bond force that is less than the first bond force of the first adhesive used to bond the flexible upper layer to the rigid substrate.

In accordance with another aspect of the invention, the valve member can be constructed as a monolithic piece of material with the flexible lower layer.

In accordance with another aspect of the invention, the valve member can be attached to the flexible lower layer via a living hinge.

In accordance with another aspect of the invention, the valve member can have an outer periphery that is severed from the material of the flexible lower layer while in the closed state.

In accordance with another aspect of the invention, the outer periphery of the valve member can be bonded to the lower surface of the rigid substrate with the second adhesive.

In accordance with another aspect of the invention, the valve member is sized for receipt in the inlet of the rigid base when in the open state.

In accordance with another aspect of the invention, a fluid storage and delivery apparatus for a disposable, point-of-care diagnostic cartridge is provided. The apparatus includes a flexible upper layer, a flexible lower layer, and a rigid substrate having an upper surface and a lower surface sandwiched between the upper and lower layers. The upper layer is fixed to the upper surface of the rigid substrate with a first adhesive having a first bond force. The upper layer has a reservoir with a fluid releasably contained therein. The rigid substrate has a through-port in fluid communication with the reservoir. The flexible lower layer has a valve member in fluid communication with the through port. The valve member has a closed state wherein the through-port is sealed off to fluid flow and an open state wherein the through-port is open to fluid flow. The valve member is moveable from the closed state to the open state under a force that is less than the first bond force of the first adhesive.

In accordance with another aspect of the invention, the valve member can be releasably bonded to the lower surface of the rigid substrate with a second adhesive having a second bond force that is less than the first bond force of the first adhesive.

In accordance with another aspect of the invention, the valve member can be constructed as a monolithic piece of material with the flexible lower layer.

In accordance with another aspect of the invention, the valve member can have an outer periphery that is severed from the material of said flexible lower layer while in the closed state.

In accordance with another aspect of the invention, a method of constructing a point-of-care diagnostic apparatus is provided. The method includes providing a rigid base; providing a flexible upper layer; providing a flexible lower layer; providing a rigid substrate, and fixing the flexible upper layer to an upper surface of the rigid substrate with a first adhesive having a first bond force, with a reservoir of the flexible upper layer having a fluid contained therein. Further, fixing the flexible lower layer to a lower surface of the rigid substrate with a valve member being registered with a through port of the rigid substrate and an inlet in the substrate. Further yet, releasably fixing the valve member in a closed state to seal off the fluid from being able to flow through the through port into the inlet, and configuring the valve member to move to an open state under a force that is less than the first bond force of the first adhesive to bring the through port and the inlet into fluid communication with one another.

In accordance with another aspect of the invention, the method can further include bonding at least a portion of the valve member to the lower surface of the rigid substrate with a second adhesive having a second bond force that is less than the first bond force of the first adhesive.

In accordance with another aspect of the invention, the method can further include forming the valve member as a monolithic piece of material with the flexible lower layer.

In accordance with another aspect of the invention, the method can further include attaching the valve member to the flexible lower layer via a living hinge.

In accordance with another aspect of the invention, the method can further include severing an outer periphery of the valve member from the material of the flexible lower layer and bonding the outer periphery to the lower surface of the rigid substrate with the second adhesive.

BRIEF DESCRIPTION OF THE DRAWINGS

These and other aspects, features and advantages of the invention will become more readily appreciated when considered in connection with the following detailed description of presently preferred embodiments and best mode, appended claims and accompanying drawings, in which:

FIG. 1A is a cross-sectional view of the diagnostic cartridge of FIG. 1 shown in a unactuated, fluid storage state;

FIG. 1B is a cross-sectional view of the diagnostic cartridge of FIG. 1 shown in an actuated, fluid dispensing state;

FIG. 3A is a cross-sectional side view of the diagnostic cartridge of FIG. 3 shown in a unactuated, fluid storage state;

FIG. 3B is a cross-sectional side view of the diagnostic cartridge of FIG. 3 shown in an actuated, fluid dispensing state;

FIG. 5 is a perspective view of a fluid storage and delivery apparatus constructed in accordance with another aspect of the invention;

FIG. 7 is an exploded view of the fluid storage and delivery apparatus of FIG. 5.

DETAILED DESCRIPTION OF PRESENTLY PREFERRED EMBODIMENTS

Figure 1:
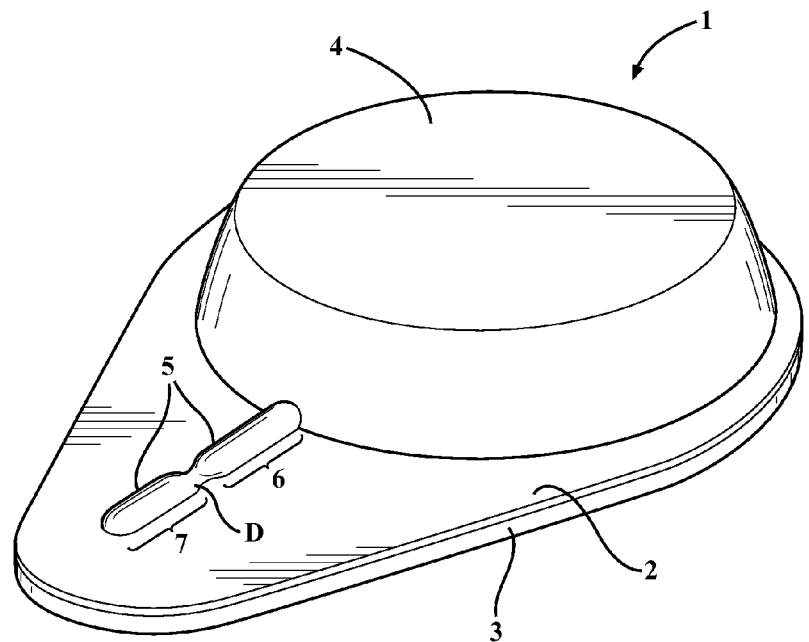
FIG. 1 is a perspective view of a diagnostic cartridge including a fluid storage and delivery apparatus constructed in accordance with the prior art.
Figure 3:
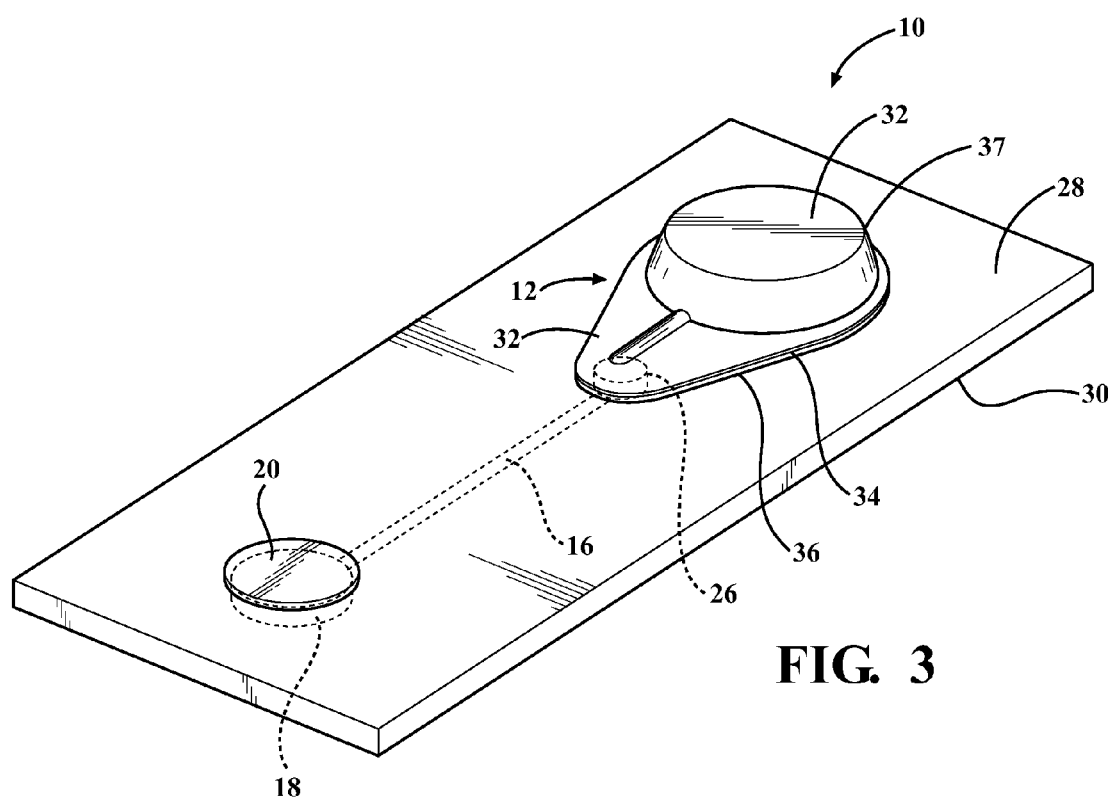
FIG. 3 is a perspective view of the diagnostic cartridge of FIG. 2.
Figure 2:
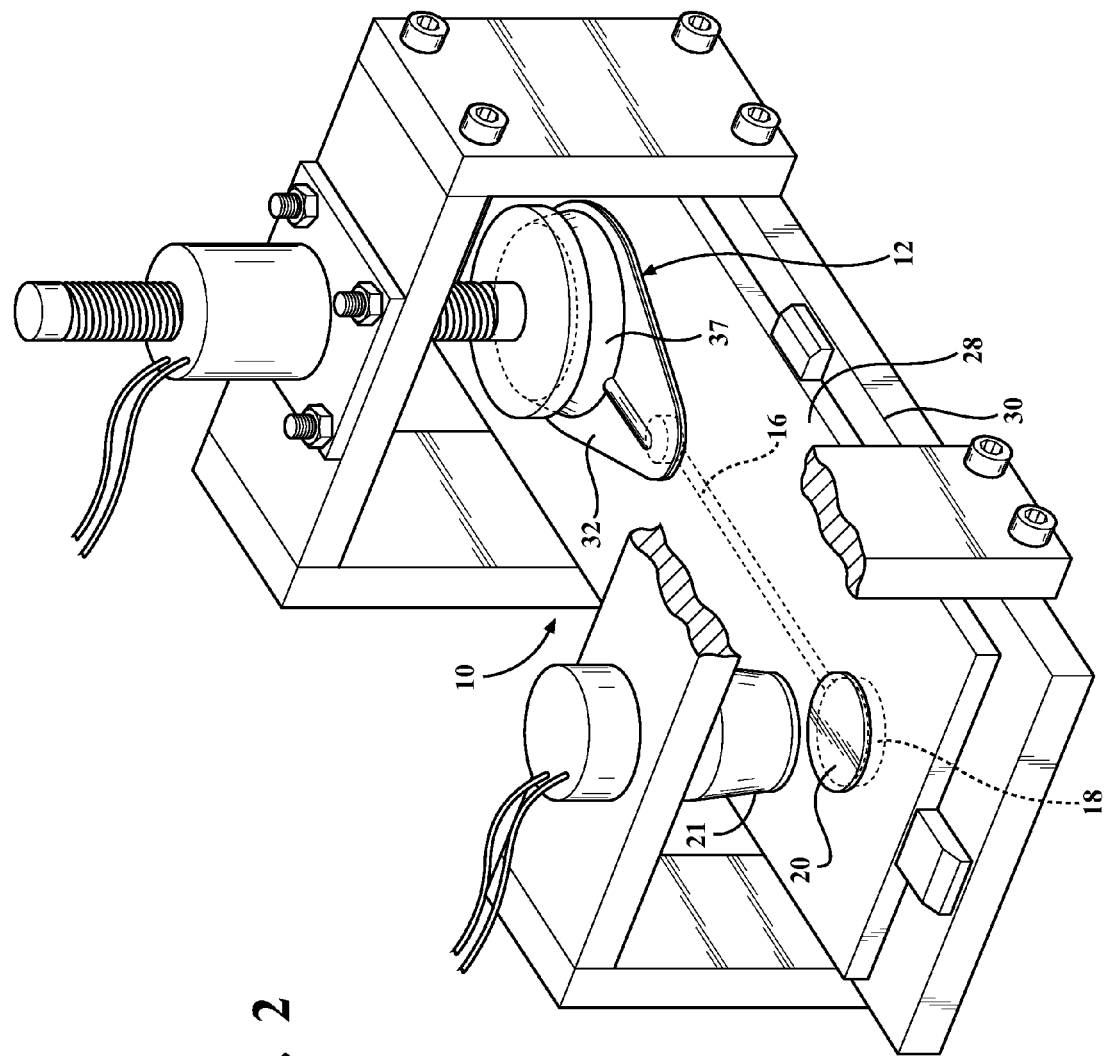
FIG. 2 is a perspective view of a diagnostic cartridge including a fluid storage and delivery apparatus constructed in accordance with one aspect of the invention shown in a actuation and analysis device.
Figure 4:
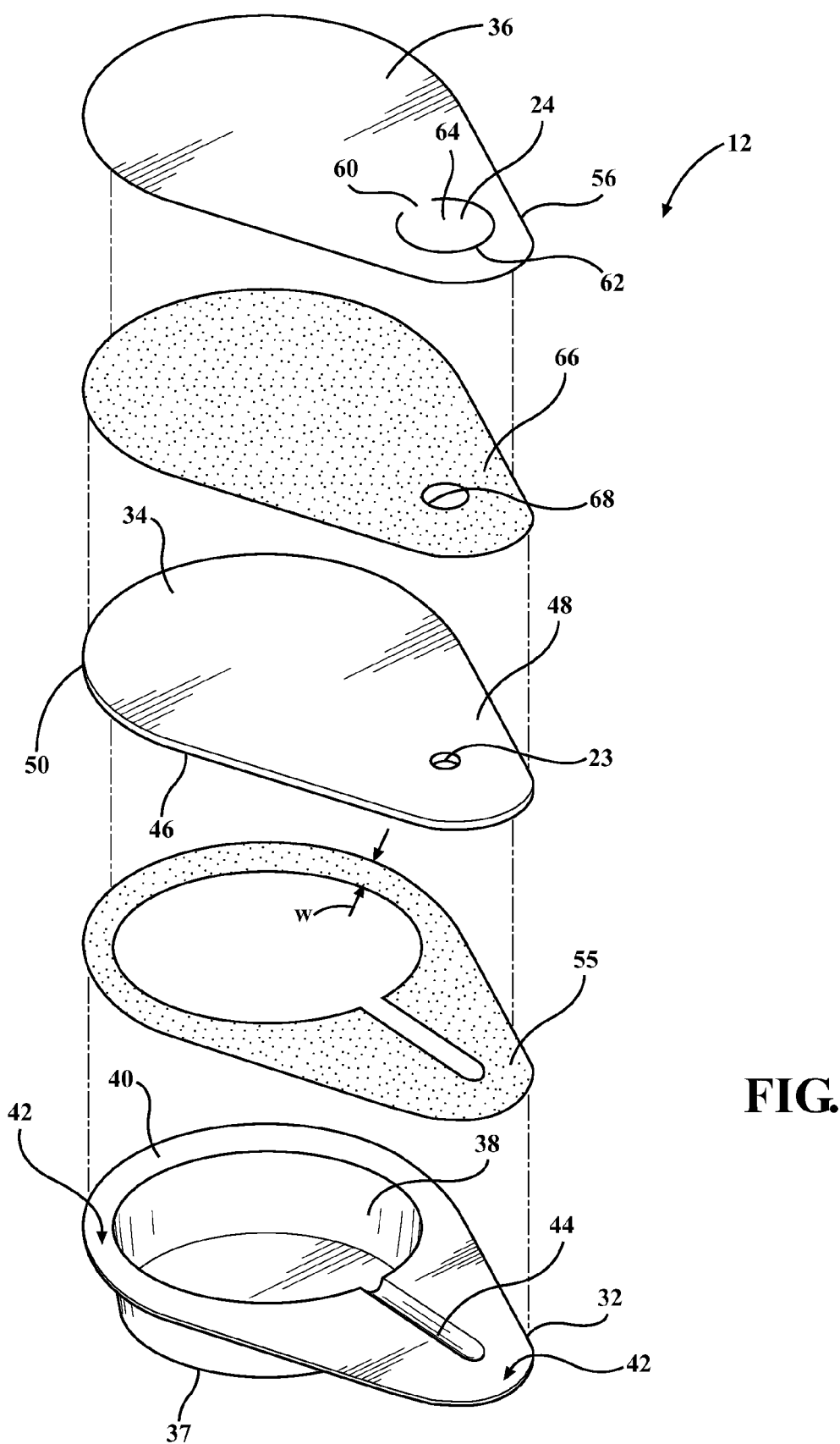
FIG. 4 is an exploded view of the fluid storage and delivery apparatus of the diagnostic cartridge of FIG. 3.

Referring in more to the drawings, FIGS. 2, 3, and 3A-B show a diagnostic cartridge 10, sometimes referred to as blister card, constructed in accordance with one aspect of the invention. The diagnostic cartridge 10 includes a fluid storage and delivery apparatus, referred to hereafter as apparatus 12, constructed in accordance with another aspect of the invention, fixed to a rigid base 14 of the diagnostic cartridge 10. The diagnostic cartridge 10, commonly referred to as a point-of-care invitro diagnostic device (IVD), is sized to be hand held and is intended to be disposable after use. The base 14 has at least one fluidic channel 16 arranged in selective, operable fluid communication with the apparatus 12 and at least one reaction chamber 18 downstream from the fluidic channel 16. The reaction chamber 18 has a viewing window 20 through which a reaction between a specimen disposed in the reaction chamber 18 and fluid 22, often referred to as a reagent, dispensed from the apparatus 12 can be viewed and analyzed via a camera 21. The apparatus 12 has an outlet port 23 arranged for fluid communication with an inlet 26 of the fluidic channel 16, wherein, to facilitate performing an accurate, reliable test, an outlet member, also referred to as valve member 24, can be reliably and selectively moved from a first, sealed closed state, wherein the outlet port is closed to fluid flow, to a second, open state, wherein the outlet port 23 is open to fluid flow, without negatively impacting the ability of the cartridge 10 to function as intended.

The base 14 is shown having opposite upper and lower surfaces 28, 30. The fluidic channel 16 is shown as extending laterally between the upper and lower surfaces 28, 30 and the viewing window 20 and inlet 26 are shown extending through the upper surface 28. The inlet 26 depends from the upper surface 28 to the fluid channel 16, which is shown as extending generally transversely from the inlet 26. As discussed, the fluidic channel 16 has a micro-sized or milli-sized diameter, while the inlet 26 has a slightly larger diameter relative to the fluidic channel 16 to facilitate introducing the fluid 22 to the fluidic channel 16 and to accommodate receipt of the outlet member 24 therein as it is biased under a sudden increase in fluid pressure to move from its closed state (FIG. 3A) to its open state (FIG. 3B).

The apparatus 12 is constructed as a composite lamination including a flexible, tear-resistant, upper film layer, shown as an uppermost layer, and referred to hereafter as blister layer 32; an intermediate, rigid substrate 34, and a flexible lower film layer, shown as a lowermost film layer 36. The blister layer 32 is shown having a generally dome-shaped bubble, commonly referred to as blister 37, wherein the blister 37 defines an annular, generally bowl-shaped chamber, also referred to as reservoir 38, with an outer peripheral flange, also referred to as lip 40, extending radially outwardly from the blister 37. The lip 40 has a lowermost, generally planar, annular joining surface, also referred to as bonding surface 42, which is fixed in bonded relation to the substrate 34. The blister 37 extends upwardly from the substrate 34 such that the fluid 22 is contained within the reservoir 38. It should be recognized that the blister 37, and thus the reservoir 38, can be sized, as desired, to contain the desired volume of the fluid 22 for the intended test, such as between 30-5000 μL, by way of example and without limitation. While the blister 37 is shown as being generally round or frustroconical, by way of example and without limitation, the lip 40 is shown as being generally teardrop-shaped, by way of example and without limitation, with an enlarged portion of the tear-drop-shaped lip 40 including a relatively narrow channel 44 extending radially outwardly from the reservoir 38 in open fluid communication with the reservoir 38. The blister layer 32 is provided as flexible, cold-formable, tough and tear-resistant material. For example, the blister layer 32 can be formed as a lamination of an outwardly facing material, including foil, such as aluminum, and an inwardly facing, fluid impervious vapor barrier, including a sheet of plastic, such as an oriented polyamide coating (oPA), with an intermediate adhesive, such as a polyvinyl chloride (PVC) or other suitable heat-activated adhesive, bonding the outer and inner laminated layers together. One such material can be purchased from Amcor Flexibles Shelbyville out of Shelbyville, Ky., USA, under the trademark FORMPACK®, under product code 15288, which is incorporated herein by reference. It should be recognized that the aforementioned materials are by way of example, and are not intended to be limiting.

The substrate 34 has respective planar or substantially planar upper and lower surfaces 46, 48 bounded by an outer periphery 50, wherein the outer periphery 50 is shown as conforming or substantially conforming in shape and size with an outer periphery of the blister layer 32, and thus, is shown as being generally teardrop-shaped, by way of example and without limitation. It should be recognized that the outer periphery 50 of the substrate 34 could take on a different shape and size than the outer periphery of the blister layer 32, as long as either the upper or lower surface 46, 48 of the substrate 34, shown as the upper surface 46, is suitably sized to allow the entire annular joining surface 42 of the blister layer 32 to be fixed thereto. To allow the fluid 22 to be selectively dispensed from the reservoir 38, the outlet port 23 that extends through the opposite upper and lower surfaces 46, 48 is arranged in open fluid communication with the reservoir 38 as a result of being aligned in open fluid communication with the channel 44.

The blister layer 32 can be fixed to the substrate 34 at an annular bond joint 54 that extends about the entirety of the lip 40 using any suitably strong fixation mechanism, including, by way of example and without limitation, welding or an adhesive having the necessary bond force properties, such as a hot melt adhesive layer 55, for example. The smallest width (W) of the bond joint 54 can be formed as narrow as about 1.5 mm, and generally ranges between about 1.5 mm-3 mm, by way of example in the smallest width region (W). Regardless of the mechanism used to fix the blister layer 32 to the substrate upper surface 46, a critical aspect of the bond joint 54 is that no fluid leak can result between the blister layer 32 and the upper surface 46 of the substrate 34 while actuating the cartridge 10 and dispensing the fluid 22 outwardly from the reservoir 38, as shown in FIG. 3B. As such, no portion of the joining surface 42 of the blister layer 32 can completely delaminate from the upper surface 46 of the substrate 34 while dispensing the fluid 22 from the reservoir 38, thereby ensuring the fluid 22 is prohibited from leaking past the bond joint 54. Simply stated, it is imperative that no fluid leak through the bond joint 54. As such, the fluid 22 is assured of being directed only through the channel 44 and through the outlet port 23, as intended, upon actuating the apparatus 12. As such, a hot melt adhesive having a first bond force, also referred to as peal force or bond strength (it is recognized that strength is generally represented as units of force/area, and thus, it is contemplated herein that the terms force and strength are relatively proportional, such that a lower bond force results in a lower bond strength, and vice versa), greater than about 25 lbf can be used for the adhesive layer 55, by way of example and without limitation.

The lowermost film layer 36 is shown as having an outer periphery 56 conforming or substantially conforming in shape and size with the outer periphery of the blister layer 32 and the outer periphery 50 of the substrate 34, and thus, is shown as being generally teardrop-shaped, by way of example and without limitation. It should be recognized that the outer periphery 56 of the lowermost film layer 36 could take on a different shape and size than the outer peripheries of both the blister layer 32 and the substrate 34, as long as the entirety of the outer periphery 56 of the lowermost film layer 36 is bonded to the lower surface 48 of the substrate 34 and completely covers the through opening forming the outlet port 23 in the substrate 34. The lowermost film layer 36 includes the valve member 24 that is selectively moveable between a sealed, closed position (FIG. 3A) and an unsealed, open position (FIG. 3B). The valve member 24 is shown, by way of example and without limitation, as being formed as a monolithic piece of material with the lowermost film layer 36, wherein the valve member 24 is moveable between the closed and open positions via a hinge, shown as a living hinge 60. The valve member 24 can take on any number of shapes, and is shown as being generally circular, thereby having an arcuate outer periphery 62. The outer periphery 62 is sized such that the entire outer periphery 62 can be bonded to the lower surface 48 of the substrate 34, along with the remaining portion of the lowermost layer 36. Of course, a central region 64 of the valve member 24 that is located directly beneath the outlet port 23 can remain free of adhesive, if desired, as it is not directly fixed to the substrate 34 due to the presence of the outlet port 23. As best shown in FIG. 3B, the valve member 24 is sized for receipt in the inlet 26 of the fluidic channel 16 upon being moved to the open position, thereby allowing the fluid 22 to flow freely out of the reservoir 38; through the outlet port 23 in the substrate 34; past the open valve member 24; through the inlet 26; through the fluidic channel 16, and into the reaction chamber 18. The valve member 24 can be formed in a cutting operation, such that the outer periphery 62 is preferably severed from the remainder of the material forming the lowermost film layer 36. Of course, the hinge 60 remains uncut, and thus, acts to couple the valve member 24 to the body of the lowermost film layer 36. It is contemplated herein that the outer periphery 62 of the valve member 24 could be formed as a weakened region, such as via a stamped, thinned region, sometimes referred to as "kiss-cut", and/or perforated region of the lowermost film layer 36, as long as the breaking or fracture force required to cause the outer periphery 62 to open is less than the bond force of the outer periphery 62 to the lower surface 48 of the substrate 34.

To ensure the valve member 24 moves from the closed position to the open position without causing a fluid leak between the blister layer 32 and the substrate upper surface 46, the valve member 24 is provided having a lower rupture strength relative to the rupture strength of the blister layer 32, as well as a lower rupture strength relative to the bond strength of the first adhesive. As such, a second adhesive 66, having a bond force, resulting in a bond strength that is less than the first bond strength of the fixation mechanism used to bond the blister layer 32 to the substrate upper surface 46, is used to bond the lowermost film layer 36, or at least the outer periphery 62 of the valve member 24, to the lower surface 48 of the substrate 34. The second adhesive 66 is shown as an adhesive layer having a through opening 68, wherein the through opening 68 is configured to register with the central region 64 of the valve member 24, thereby avoiding bringing the fluid 22 into contact with the second adhesive 66 prior to movement of the valve member 24 from the closed position to the open position. As such, upon application of a crush force to the blister 37, the outer periphery 62 of the valve member 24 is caused to intentionally delaminate from the lower surface 48 of the substrate 34 under the force of the fluid 22, while the entirety of the bond joint 54 between the blister layer 32 and the upper surface 46 of the substrate 34 remains intact. In accordance with a preferred embodiment, the force required to cause the valve member 24 to move from the bonded, closed position (FIG. 3A) to the unbonded, open position (FIG. 3B) is less than about 15 lbf, and preferably less than 10 lbf, and more preferably between about 2-8 lbf, by way of example and without limitation, and thus, the risk of a leak forming between the blister layer 32 and the substrate 34 is negated. Furthermore, with the force required to open the valve member 24 being relatively low, the phenomenon of a sudden "in-rush" of the fluid 22 through the inlet 26 is avoided.

In FIG. 5, a fluid storage and delivery apparatus, referred to hereafter as apparatus 112, constructed in accordance with another aspect of the invention, is shown, wherein the same reference numerals as used above, offset by a factor of 100, are used to identify like features. The apparatus 112 is fixed to a rigid base 114 of a diagnostic cartridge 110, wherein the rigid base 114 is substantially the same as described above for the base 14. Accordingly, the base 114 has at least one fluidic channel 116 arranged in selective, operable fluid communication with the apparatus 112 via an inlet 126, as well as with at least one reaction chamber 118 downstream from the fluidic channel 116.

As best shown in FIG. 7, the apparatus 112 includes a blister layer 132 having a bulbous blister 137 providing a reservoir 138 for releasably stored containment of a reagent fluid 122; a rigid substrate 134 having an outlet port 123; and a lower film layer 136 providing a valve or outlet member 124, wherein the rigid substrate 134 is sandwiched between the blister layer 132 and the lower film layer 136, as described above for the apparatus 12. As with the apparatus 12 discussed above, the outlet member 124 is configured to open under a significantly less force than required to delaminate the blister layer 132 from the substrate 134, and as such, the apparatus 110 is assured to function as intended.

Figure 6A:
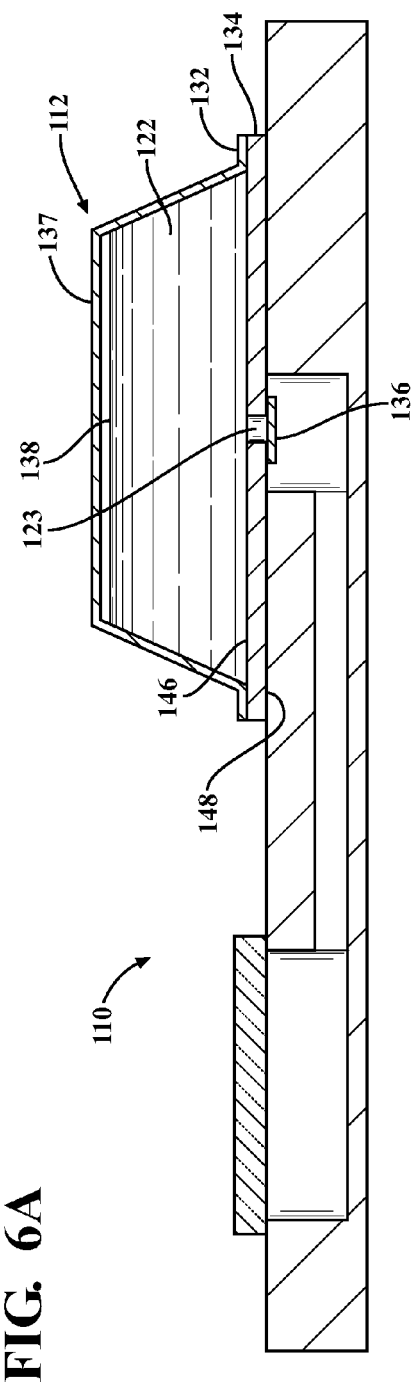
FIG. 6A is a cross-sectional side view of a diagnostic cartridge including the fluid storage and delivery apparatus of FIG. 5 shown in a unactuated, fluid storage state.
Figure 6B:
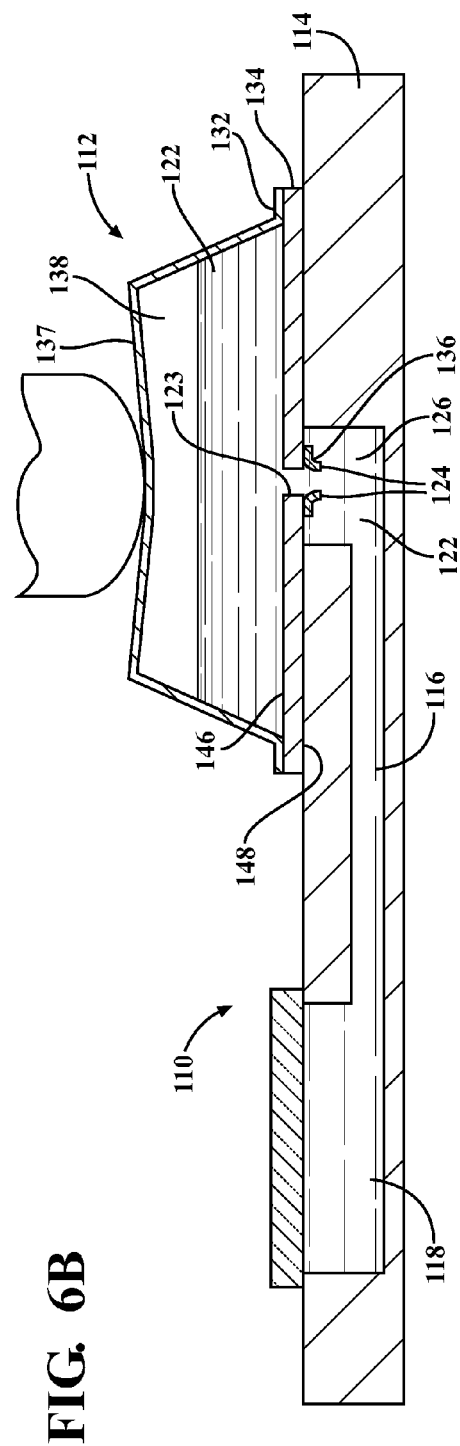
FIG. 6B is a cross-sectional side view of the diagnostic cartridge of FIG. 6A shown in an actuated, fluid dispensing state.

The blister layer 132, rather than being teardrop-shaped, as with the blister layer 32, is shown as being round, by way of example and without limitation, and can be formed from the same material discussed above for the blister layer 32. The blister layer 132 is shown as being bonded to an upper surface 146 of the substrate 134 via a ring of a first adhesive 155, such as from the same adhesive material 55 discussed above, and is shown as being centered with respect to the outlet port 123, by way of example and without limitation. In addition, the lower film layer 136 is also bonded to a lower surface 148 of the substrate 134 via a second adhesive 166 having a through opening 168, wherein the through opening 168 is configured to register with the through opening 123, thereby avoiding or minimizing the volume of the fluid 122 that can contact the second adhesive 166 prior to movement of the valve member 124 from the closed position (FIG. 6A) to the open position (FIG. 6B). In contrast to the first embodiment, the second adhesive 166 can be provided as the same adhesive as used to the bond the blister layer 132 to the substrate 134. Accordingly, during actuation of the apparatus 112, both the blister layer 132 and the lower film layer 136 remain bonded to their respective surfaces 146, 148 of the substrate 134 about their entire peripheries. As such, the outlet member 124, in contrast to the outlet member 24, is not opened as a result of a lesser bond strength of the second adhesive 166, but rather, it opens as a function of the outlet member 24 in the lower film layer 136 having a reduced rupture strength relative to the rupture strength of the blister layer 132. The reduced strength of the valve member 124 can be provided as a result of the lower film layer 136 having a reduced elasticity and material strength in its entirety relative to the elasticity and material strength of the blister layer 132, or the valve member 124 can itself have a reduced strength, such as by being formed having a thinned region or regions of material selectively formed in the lower film layer 136. If the valve member 124 is formed having at least one thinned region, the at least one thinned region can be produced via any suitable manufacturing process, such as via die stamping, embossing, kiss cutting, scoring, or the like, thereby intentionally forming precisely controlled and precisely located weakened regions 70 in the lower film layer 136. The lowermost film layer 136 can be provided as a push-through type material, such as those used in medication packages, for example, and can be purchased from Amcor Flexibles Shelbyville out of Shelbyville, Ky., USA, under the product code PFH-092, specification number 10038, which is incorporated herein by reference.

During actuation of the cartridge 110, upon depressing the blister 137, the valve member 124 is caused to rupture or open prior to any substantial delamination of the blister layer 132 from the substrate 134. Accordingly, the blister layer 132 is assured of remaining in a leak-free bond with the substrate 134. Meanwhile, the valve member 124 is assured of opening, as intended, as a result of the aforementioned relatively weak strength of the valve member 124, whether as a result of a relatively weak material rupture strength and/or a relatively weak rupture strength imparted by intentionally weakened regions 70 within the lower layer 136 in comparison to the relatively strong material strength of the blister layer 132, and also the relatively strong bond strength of the first adhesive 155.

In accordance with another aspect of the invention, a method of constructing the apparatus 10 is provided. The method includes providing the rigid base 14, 114, as detailed above; providing the flexible upper layer 32, 132, as detailed above; providing the flexible lower layer 36, 136, as detailed above; providing the rigid substrate 34, 134, as detailed above, and fixing the flexible upper layer 32, 132 to the upper surface 46, 146 of the rigid substrate 34, 134 with a first adhesive 55, 155 having a first bond force, resulting in first bond strength, with the reservoir 38, 138 having a fluid 22, 122 releasably contained therein, wherein the fluid 22, 122 is in fluid communication with the through port 23, 123 of the rigid substrate 34, 134. Further, fixing the flexible lower layer 36, 136 to the lower surface 48, 148 of the rigid substrate 34, 134 with the valve member 24, 124 being registered with the through port 23, 123 and the inlet 26, 126 of the fluidic channel 16, 116 in the substrate 34, 134. Further yet, releasably fixing the valve member 24, 124 in a closed state to seal off the fluid 22, 122 from being able to flow through the through port 23, 123 into the inlet 26, 126, and configuring the valve member 24, 124 to move to an open state under a force that is less than the first bond force of the first adhesive 55, 155 to bring the through port 23, 123 and the inlet 26, 126 into fluid communication with one another.

The method can further include bonding at least a portion of the valve member 24 to the lower surface 48 of the rigid substrate 34 with a second adhesive 66 having a second bond force and corresponding bond strength that is less than the first bond force and corresponding bond strength of the first adhesive 55.

The method can further include forming the valve member 24, 124 as a monolithic piece of material with the flexible lower layer 36, 136.

The method can further include attaching the valve member 24 to the flexible lower layer 36 with a living hinge 60.

The method can further include severing an outer periphery 62 of the valve member 24 from the material of the flexible lower layer 36 and bonding the outer periphery 62 to the lower surface 48 of the rigid substrate 34 with the second adhesive 66.

The method can further include forming the valve member 124 having a reduced rupture strength relative to the rupture strength of the flexible upper layer 132.

The method can further include forming the valve member 124 having thinned regions 70 to reduce the rupture strength of the valve member 124.

Many modifications and variations of the present invention are possible in light of the above teachings. It is, therefore, to be understood that the invention may be practiced otherwise than as specifically described, and that the scope of the invention is defined by any ultimately allowed claims.

What is claimed is:

1. A disposable, point-of-care diagnostic cartridge, comprising:

a rigid base having opposite upper and lower surfaces with a reaction chamber between said upper and lower surfaces and an inlet extending into said upper surface with at least one fluidic channel extending between said reaction chamber and said inlet in fluid communication with said reaction chamber and said inlet;

a fluid storage and delivery apparatus fixed to said upper surface of said rigid base, said fluid storage and delivery apparatus including a flexible upper layer, a flexible lower layer, and a rigid substrate having an upper surface and a lower surface sandwiched between said upper and lower layers, said upper layer being fixed to said upper surface of said rigid substrate with a first adhesive having a first bond force, said upper layer having a reservoir with a fluid releasably contained therein, said rigid substrate having a through port in fluid communication with said reservoir, said flexible lower layer having a valve member in fluid communication with said through port and said inlet of said rigid base, said valve member having a closed state wherein said through port and said inlet are sealed off from fluid communication with one another and an open state wherein said through port and said inlet are in fluid communication with one another, said valve member being moveable from said closed state to said open state under a force that is less than said first bond force.

2. The disposable, point-of-care diagnostic cartridge of claim 1 wherein said valve member is releasably bonded to said lower surface of said rigid substrate with a second adhesive having a second bond force, said second bond force being less than said first bond force.

3. The disposable, point-of-care diagnostic cartridge of claim 2 wherein said valve member is constructed as a monolithic piece of material with said flexible lower layer.

4. A disposable, point-of-care diagnostic cartridge, comprising:
a rigid base having opposite upper and lower surfaces with a reaction chamber between said upper and lower surfaces and an inlet extending into said upper surface with at least one fluidic channel extending between said reaction chamber and said inlet in fluid communication with said reaction chamber and said inlet;
an apparatus fixed to said upper surface of said rigid base, said apparatus including a flexible upper layer, a flexible lower layer, and a rigid substrate having an upper surface and a lower surface sandwiched between said upper and lower layers, said upper layer being fixed to said upper surface of said rigid substrate with a first adhesive having a first bond force, said upper layer having a reservoir with a fluid releasably contained therein, said rigid substrate having a through port in fluid communication with said reservoir, said flexible lower layer having a valve member in fluid communication with said through port and said inlet of said rigid base, said valve member having a closed state wherein said through port and said inlet are sealed off from fluid communication with one another and an open state wherein said through port and said inlet are in fluid communication with one another, said valve member being moveable from said closed state to said open state under a force that is less than said first bond force;
wherein said valve member is releasably bonded to said lower surface of said rigid substrate with a second adhesive having a second bond force, said second bond force being less than said first bond force;
wherein said valve member is constructed as a monolithic piece of material with said flexible lower layer; and
wherein said valve member is attached to said flexible lower layer via a living hinge.

5. The disposable, point-of-care diagnostic cartridge of claim 4 wherein said valve member has an outer periphery that is severed from the material of said flexible lower layer.

6. The disposable, point-of-care diagnostic cartridge of claim 5 wherein said outer periphery of said valve member is bonded to said lower surface of said rigid substrate with said second adhesive.

7. The disposable, point-of-care diagnostic cartridge of claim 5 wherein said valve member is sized for receipt in said inlet of said rigid base when in said open state.

8. The disposable, point-of-care diagnostic cartridge of claim 1 wherein said flexible lower layer is bonded to said lower surface of said rigid substrate with a second adhesive having a second bond force, said second bond force being less than said first bond force.

9. A fluid storage and delivery apparatus for a disposable, point-of-care diagnostic cartridge, comprising:
a flexible upper layer, a flexible lower layer, and a rigid substrate having an upper surface and a lower surface sandwiched between said upper and lower layers, said upper layer being fixed to said upper surface of said rigid substrate with a first adhesive having a first bond force, said upper layer having a reservoir with a fluid releasably contained therein, said rigid substrate having a through port in fluid communication with said reservoir, said flexible lower layer having a valve member in fluid communication with said through port, said valve member having a closed state wherein said through port is sealed off to fluid flow and an open state wherein said through port is open to fluid flow, said valve member being moveable from said closed state to said open state under a force that is less than said first bond force.

10. The fluid storage and delivery apparatus of claim 9 wherein said valve member is releasably bonded to said lower surface of said rigid substrate with a second adhesive having a second bond force, said second bond force being less than said first bond force.

11. The fluid storage and delivery apparatus of claim 10 wherein said valve member is constructed as a monolithic piece of material with said flexible lower layer.

12. The fluid storage and delivery apparatus of claim 11 wherein said valve member has an outer periphery that is severed from the material of said flexible lower layer.

13. The fluid storage and delivery apparatus of claim 9 wherein said flexible lower layer is bonded to said lower surface of said rigid substrate with a second adhesive having a second bond force, said second bond force being less than said first bond force.

14. A disposable, point-of-care diagnostic cartridge, comprising:
a rigid base having opposite upper and lower surfaces with a reaction chamber between said upper and lower surfaces and an inlet extending into said upper surface with at least one fluidic channel extending between said reaction chamber and said inlet in fluid communication with said reaction chamber and said inlet;
a fluid storage and delivery apparatus fixed to said upper surface of said rigid base, said fluid storage and delivery apparatus including a flexible upper layer, a flexible lower layer, and a rigid substrate having an upper surface and a lower surface sandwiched between said upper and lower layers, said upper layer being fixed to said upper surface of said rigid substrate with a first adhesive, said upper layer having a reservoir with a fluid releasably contained therein, said rigid substrate having a through port in fluid communication with said reservoir, said flexible lower layer having a valve member in fluid communication with said through port and said inlet of said rigid base, said valve member having a closed state wherein said through port and said inlet are sealed off from fluid communication with one another and an open state wherein said through port and said inlet are in fluid communication with one another; and wherein said valve member is releasably bonded to said lower surface of said rigid substrate with a second adhesive, wherein said valve member is attached to said flexible lower layer via a living hinge.

* * * * *